United States Patent [19]
Cunningham et al.

[11] Patent Number: 6,092,429
[45] Date of Patent: Jul. 25, 2000

[54] DRIVER FOR OSCILLATING A VIBRATING CONDUIT

[75] Inventors: Timothy J. Cunningham, Boulder, Colo.; Stuart J. Shelley, Cincinnati, Ohio

[73] Assignee: Micro Motion, Inc., Boulder, Colo.

[21] Appl. No.: 08/984,927

[22] Filed: Dec. 4, 1997

[51] Int. Cl.[7] .................................................. G01F 1/78
[52] U.S. Cl. ...................................................... 73/861.356
[58] Field of Search ...................... 73/861.355, 861.356, 73/861.357

[56] References Cited

U.S. PATENT DOCUMENTS

| | | | |
|---|---|---|---|
| 4,422,338 | 12/1983 | Smith | 73/861.38 |
| 4,777,833 | 10/1988 | Carpenter | 73/861 |
| 4,823,614 | 4/1989 | Dahlin | |
| 5,009,109 | 4/1991 | Kalotay et al. | 73/861.37 |
| 5,301,557 | 4/1994 | Cage et al. | 73/861 |
| 5,734,112 | 3/1998 | Bose et al. | 73/861.56 |

FOREIGN PATENT DOCUMENTS

| | | | |
|---|---|---|---|
| 0 578 113 A2 | 1/1984 | European Pat. Off. | G01F 1/84 |
| 0 361 388 A2 | 4/1990 | European Pat. Off. | |
| 0 701 107 A2 | 3/1996 | European Pat. Off. | G01F 1/00 |
| WO 92/14123 | 8/1992 | WIPO | G01F 1/84 |
| WO 95/29385 | 2/1995 | WIPO | G01F 1/84 |
| WO 95/16897 | 6/1995 | WIPO | G01F 1/84 |
| WO 97/40348 | 10/1997 | WIPO | G01F 1/84 |
| WO 98/07009 | 2/1998 | WIPO | G01F 1/84 |

OTHER PUBLICATIONS

Cunningham; "Zero Shifts Due to Non–Proportional Damping", Micro Motion Report #10233, Part of IMAC XV, Feb. 1997; Session 8j, Structural Damping.

Bosse et al.; "Application of Modal Filtering Techniques to Vibration Control of Precision Truss", AD–VOL. 45/MD–VOL. 54, Adaptive Structures and Composite Material, Analysis and Application ASME 1994, pp. 281–285.

Cunningham; "Zero Shifts in Coriolis Sensors Due to Imbalance", Proceedings of AIAA/ASME/ASCE/AHS/ASC 35th Structures, Structural Dynamics and Materials Conference, Apr. 18–20, 1994, AIAA Paper 94–1621 (A94–2411a).

Stack, Garnett, Pawlas; "A Finite Element for the Vibration Analysis of Fluid–Conveying Timoshenko Beam", AIAA Paper 93–1552, pp. 1–10 (1993).

Rieder, Drahm; "A New Type of Single Straight Tube Coriolis Mass Flowmeter", Flomenko '96, presented at the 8th International Conference (1996), p. 250–255.

Stuart J. Shelley, Investigation of Discrete Modal Filters For Structural Dynamic Applications (1991) (Unpublished Ph. D. Dissertation, University of Cincinnati).

Garnett et al., "A Finite Element for the Vibration Analysis of a Fluid–Conveying Timoshenko Beam," AIAA, American Inst. of Aeronautics and Astronautics, Inc., p. 2120–2129, (1993).

*Primary Examiner*—Benjamin R. Fuller
*Assistant Examiner*—Jewel V. Thompson
*Attorney, Agent, or Firm*—Duft, Graziano & Forest, P.C.

[57] ABSTRACT

A process parameter measurement device, and in particular a Coriolis mass flowmeter or vibrating tube densimeter, having a driver or drivers for inducing oscillation of at least one conduit. The drivers are attached at locations along the vibrating conduit selected to influence certain modes of interest. A driver is located near an area of maximum amplitude of a desired vibration mode and near an area of minimum amplitude of an undesired vibration mode. Various known experimental modal analysis or modeling techniques are used to determine the appropriate locations for one or more drivers. Multiple drivers located according to the present invention are used to influence, i.e., excite or suppress, multiple modes. In addition, multiple, separate drive circuits produce multiple, electronically isolated drive signals for delivering greater total power to the vibrating conduit.

25 Claims, 10 Drawing Sheets

DRIVER FOR OSCILLATING A VIBRATING CONDUIT

FIELD OF THE INVENTION

The present invention relates to apparatus and methods of utilizing and controlling a driver(s) for oscillating a vibrating conduit. More particularly the present invention relates to optimally locating a driver(s) so that multiple vibration modes are appropriately influenced by operation of the driver(s).

STATEMENT OF THE PROBLEM

It is known to use Coriolis effect mass flowmeters to measure mass flow and other information for materials flowing through a conduit. Exemplary Coriolis flowmeters are disclosed in U.S. Pat. Nos. 4,109,524 of Aug. 29, 1978, 4,491,025 of Jan. 1, 1985, and Re. 31,450 of Feb. 11, 1982, all to J. E. Smith et al. These flowmeters have one or more conduits of straight or curved configuration. Each conduit configuration in a Coriolis mass flowmeter has a set of natural vibration modes, which may be of a simple bending, torsional, radial or coupled type. Each conduit is driven to oscillate at resonance in one of these natural modes. Material flows into the flowmeter from a connected conduit on the inlet side of the flowmeter, is directed through the conduit or conduits, and exits the flowmeter through the outlet side. The natural vibration modes of the vibrating, material filled system are defined in part by the combined mass and stiffness characteristics of the conduits and the material flowing within the conduits.

When there is no flow through the flowmeter, all points along the conduit oscillate, due to an applied driver force, with identical phase or a zero-flow phase depending on the mode of the driven vibration. As material begins to flow, Coriolis forces cause a change in phase difference between any two points along the conduit. The phase on the inlet side of the conduit lags the driver, while the phase on the outlet side leads the driver. Pick-off sensors are placed on the conduit to produce sinusoidal signals representative of the motion of the conduit. Signals output from the pick-off sensors are processed to determine the change in phase difference between the pick-off sensors. The change in phase difference between two pick-off sensor signals is proportional to the mass flow rate of material through the conduit.

A typical component of every Coriolis flowmeter, and of every vibrating tube densitometer, is the drive or excitation system. The drive system operates to apply a periodic physical force to the conduit which causes the conduit to oscillate. The drive system includes a driver mounted to the conduit(s) of the flowmeter. The driver mechanism typically contains one of many well known arrangements, such as, but not limited to, a voice coil where a magnet is mounted to one conduit and a wire coil is mounted to the other conduit in an opposing relationship to the magnet. A drive circuit continuously applies a periodic, typically sinusoidally or square shaped, drive signal to the driver coil. Through interaction of the continuous alternating magnetic field produced by the coil in response to the periodic drive signal and the constant magnetic field produced by the magnet, both flow conduits are initially forced to vibrate in an opposing sinusoidal pattern which is thereafter maintained. Those skilled in the art recognize that any device capable of converting an electrical signal to mechanical force is suitable for application as a driver. (See U.S. Pat. No. 4,777,833 issued to Carpenter and assigned on its face to Micro Motion, Inc.) Also, one need not use a sinusoidal signal but rather any periodic signal may be appropriate as the driver signal (see U.S. Pat. No. 5,009,109 issued to Kalotay et. al. and assigned on its face to Micro Motion, Inc.).

A typical mode, although not the only mode, in which a dual-tube Coriolis flowmeter is driven is the first out-of-phase bending mode. However, the first out-of-phase bending mode is not the only mode of vibration present in the vibrating structure of a Coriolis flowmeter driven in the first out-of-phase bending mode. There are, of course, higher modes of vibration which may be excited. There are also, as a result of fluid flowing through the vibrating conduit and the consequent Coriolis forces, Coriolis response modes such as the first out-of-phase twist mode. There are also in-phase and lateral modes of vibration. Other reasons that additional and undesirable modes are sometimes excited in a Coriolis flowmeter is when manufacturing tolerances are such that the driver elements are not located symmetrically on the conduits or the driver does not generate a pure uni-axial force in the intended direction perpendicular to the tube plane. This results in the driver putting eccentric forces into the conduits hence exciting multiple modes of vibration. In addition to multiple modes being excited by the driven excitation of the conduits, modes can be excited due to vibrations external to the flowmeter. For example, a pump located elsewhere in a process line might generate a vibration along a pipeline that excites a mode of vibration in a Coriolis flowmeter. Ultimately, there are hundreds of vibration modes present in a Coriolis flowmeter that is intended to oscillate in only a single mode such as the first out-of-phase bending mode. Even within a relatively narrow range of frequencies near the driven mode there are typically at least several additional modes of vibration. Thus a Coriolis flowmeter driven to oscillate or resonate at one mode actually has a conduit(s) oscillating in many other modes in addition to the intended mode.

The pick-off sensors on a vibrating conduit(s) produce feedback signals representative of the vibration of the conduit(s). Thus if the conduit(s) are vibrating at multiple modes then any feedback signal from a pick-off sensor on the vibrating conduit(s) will have modal content representative of the multiple modes of vibration. This can lead to problems in the drive signal feedback loop since undesired vibration modes can be reinforced by the drive signal itself. For example, a pump might cause a vibration in a pipeline in which is fixed a Coriolis flowmeter. The Coriolis flowmeter is caused to vibrate at a certain mode because of the pump vibration. This vibration mode is represented by certain modal content in the drive feedback signal (from one of the pick-offs). The drive feedback signal is processed to produce a drive signal. The drive signal, which still has modal content at the vibration mode induced by the pump vibration, is used to drive the Coriolis flowmeter to vibrate. Thus the flowmeter is driven to vibrate at an undesirable mode.

Another exemplary problem relates to intrinsic safety requirements. In order to meet intrinsic safety requirements set by various approvals agencies, the total power available at the driver of a Coriolis flowmeter is limited. This power limitation can be a problem for Coriolis flowmeters particularly with respect to larger flowmeters and more particularly with respect to larger flowmeters measuring fluids with entrained gas. Therefore it is important to input energy to a flowmeter in a way that only the desired vibration mode(s) is excited therefore inputting energy at the desired modes and not 'wasting' energy on undesired modes.

A further problem is that, in the example of an historical Coriolis meter driven at the first out-of-phase bend mode, the driver location is also a position of maximum amplitude for the second out-of-phase bend mode. Hence the second out-of-phase bend mode is solidly excited in a Coriolis meter driven to oscillate at the first out-of-phase bend mode. The drive feedback signal, and subsequently the drive signal, therefore contains a strong response in the second out-of-phase bend mode.

U.S. Pat. No. 5,301,557 issued Apr. 12, 1994 to Cage et al. and assigned on its face to Micro Motion, Inc. ("the '557 patent") describes a method of locating pick-off sensors on the conduit(s) of a Coriolis flowmeter. The '557 patent describes a method for mounting pick-offs at locations on a conduit(s) near a node(s) of an undesired mode(s) of vibration. The pick-offs are therefore less likely to produce signals having a strong component of the undesired mode(s). The '557 patent does not teach anything about the placement of drivers or use of the drive signal where undesired modes are suppressed.

There is a need for optimally locating driver elements on the vibrating tube(s) so that unwanted modes are minimized. There exists a further need for increasing the driver force available at a Coriolis flowmeter while still complying with intrinsic safety requirements. There exists a need for influencing multiple modes on the vibrating tube(s) of a flowmeter such as to excite two modes or to excite one mode and suppress another.

STATEMENT OF THE SOLUTION

The above identified problems, and others, are solved and a technical advance is achieved in the field by the drive system of the present invention. The present invention provides a method and apparatus for using modal analysis techniques to optimally locate a driver(s) on the vibrating tube(s) of a flowmeter so that vibration modes are appropriately influenced. One or more drivers are placed at location(s) on the conduit(s) such that energy is input to the vibrating structure that excites a desired vibration mode(s) and does not excite an undesired vibration mode(s). Excitation of undesired modes is minimized, driver force at the desired vibration mode is maximized, and conduit(s) are thereby more effectively driven in the desired mode(s).

A method is provided for optimally locating drivers on the vibrating conduits so that influence of multiple vibration modes is controlled. To influence a mode is to excite or suppress the mode. A Finite Element (FE) model of the vibrating conduit(s) is built. The eigenvector coefficients for the modes of interest are extracted from the FE model. Alternatively, modal analysis techniques are used to determine the eigenvector coefficients for the modes of interest. The eigenvector coefficients of the modes of interest are graphed to identify those regions along the vibrating tube(s) where, for example, one desired mode is near a point of maximum amplitude and one undesired mode is near a point of minimum amplitude. A driver is positioned within this region. A driver located in this region is less likely to excite the undesired mode while appropriately exciting the desired mode. The same technique is used to locate a driver(s) so that multiple desired modes are most effectively excited or to ensure that multiple undesired modes are not excited.

The eigenvector coefficients for the modes of interest are alternatively used to produce a Frequency Response Function (FRF) for the vibrating conduit(s). A FRF characterizes the dynamics between a force applied to a structure at one location and the resulting motion of the structure at another location. The FRF is used to quantitatively determine the optimal driver location(s) on the vibrating tube(s) as an alternative to the graphing method noted above.

A U-shaped vibrating conduit provides an example of the present invention for optimally locating drivers. Historically a single driver is located at the center of the bight end of a U-shaped conduit. A sinusoidal signal at the frequency of the first out-of-phase bend mode is delivered to the single driver to cause the conduit(s) to vibrate. The center of the bight end of the conduit(s) is a point of maximum amplitude of both the first and second out-of-phase bend modes of the U-shaped conduit(s). Thus, this driver location tends to excite the undesirable second out-of-phase bending mode as well as the desirable first out-of-phase bending mode. The present invention provides a flowmeter with driver(s) located at position(s) such that the first out-of-phase bend mode is excited (desirable) but excitation of the second out-of-phase bend mode is minimized. This is accomplished according to the present invention by placing at least one driver at a location which is near a position of maximum amplitude of the desired first out-of-phase bend mode and near a position of minimum amplitude of the undesired second out-of-phase bend mode.

A further example of the present invention is where one desires to excite both the first out-of-phase bend mode and the first out-of-phase twist mode but not the second out-of-phase bend mode. Historically, this would be accomplished by locating, in the example of a U-shaped conduit(s), a single driver at the center of the bight end of the conduit to excite the first out-of-phase bend mode and a pair of drivers on opposite legs of the conduit(s) to excite the first out-of-phase twist mode. An entirely different approach and structure result according to the present invention. A FE model of the vibrating structure is built. The eigenvector coefficients for the first out-of-phase bend mode, first out-of-phase twist mode and second out-of-phase bend mode are extracted from the FE model. The eigenvector coefficients are graphed with respect to distance along the conduit and the driver locations are selected. The selected driver locations are positions along the conduit where the first out-of-phase bend mode and the first out-of-phase twist mode are near points of maximum amplitude and the second out-of-phase bend mode is near a point of minimum amplitude. Thus appropriately phased energy input to the drivers at these locations tends to excite the first out-of-phase bend mode and the first out-of-phase twist mode and likewise tends not to excite the second out-of-phase bend mode.

Optimal location of drivers also allows for an increase in the power input to the vibrating tube(s) at the desired mode(s) since more of the available power is delivered at the desired mode(s). This is advantageous where high drive power is necessary such as, but not limited to, where intrinsic safety requirements are an issue. Further gains in drive power are achievable according to the present invention by using multiple drivers, which are appropriately located and each of which is controlled by a separate drive circuit.

DETAILED DESCRIPTION

Figure 1:
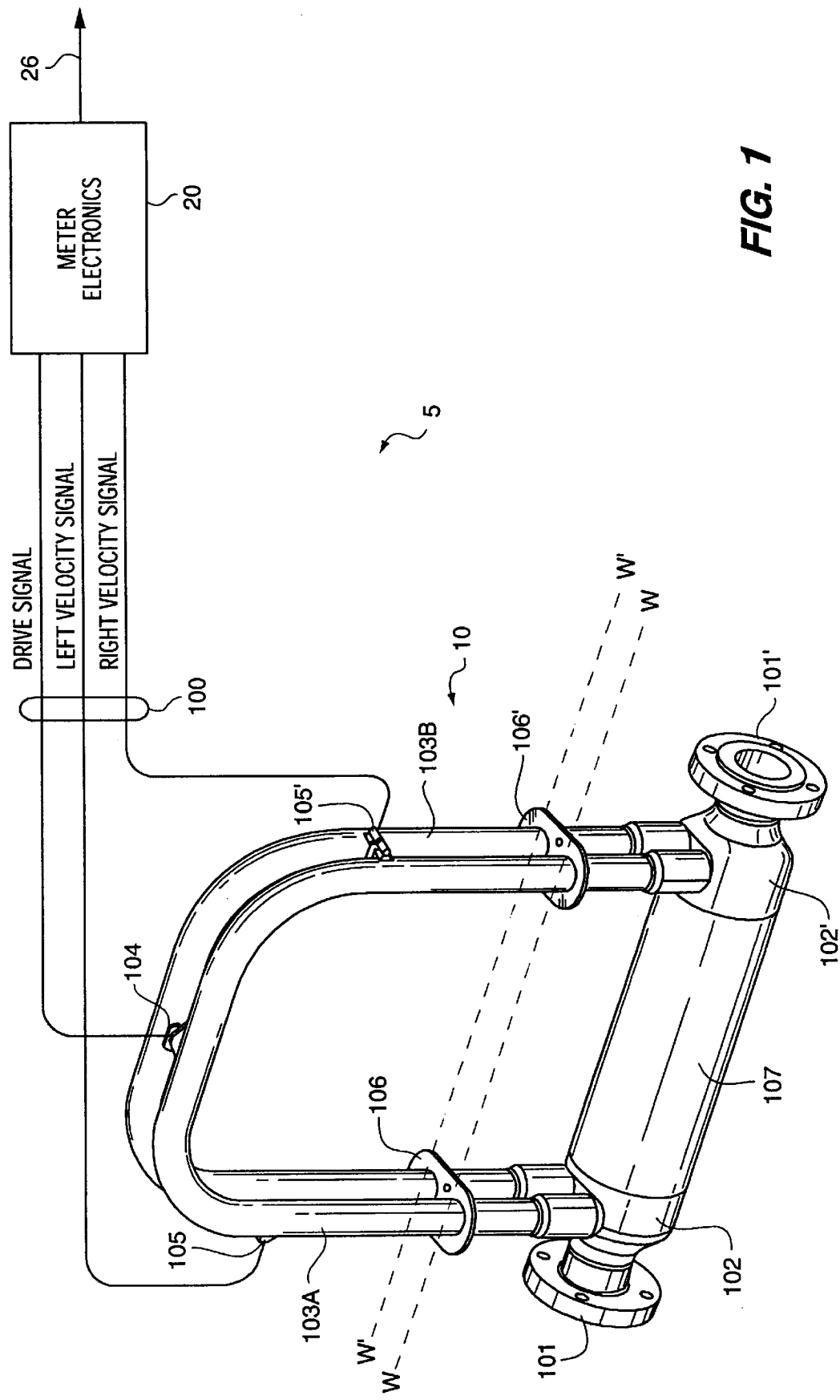
FIG. 1 depicts a Coriolis mass flowmeter system.

Coriolis Flowmeter System in General—FIG. 1

FIG. 1 shows a Coriolis flowmeter 5 comprising a Coriolis meter assembly 10 and meter electronics 20. Meter electronics 20 is connected to meter assembly 10 via leads 100 to provide density, mass flow rate, volume flow rate and totalized mass flow information over path 26. FIGS. 1–8 depict the structure and operation of a model CMF300 Coriolis mass flowmeter manufactured by Micro Motion, Inc. of Boulder, Colo. A certain Coriolis flowmeter structure is described although it is apparent to those skilled in the art that the present invention could be practiced in conjunction with a vibrating tube densitometer without the additional measurement capability provided by a Coriolis mass flowmeter. Also, although certain Coriolis flowmeter configurations are shown and described herein, those skilled in the art of vibrating tube sensors recognize that the present invention is equally applicable to any vibrating tube flowmeter or densitometer regardless of the number and shape of the vibrating conduits. In essence, the present invention is applicable to any process parameter measurement device that employs a vibrating conduit.

Meter assembly 10 includes a pair of flanges 101 and 101', manifolds 102, 102; spacer 107 and conduits 103A and 103B. Connected to conduits 103A and 103B are driver 104 and pick-off sensors 105 and 105'. Brace bars 106 and 106' serve to define the axis W and W' about which each conduit oscillates.

When flowmeter 10 is inserted into a pipeline system (not shown) which carries the process material that is being measured, material enters meter assembly 10 through flange 101, passes through manifold 102 where the material is directed to enter conduits 103A and 103B, flows through conduits 103A and 103B and back into manifold 102 from where it exits meter assembly 10 through flange 101'.

Conduits 103A and 103B are selected and appropriately mounted to the manifold 102 so as to have substantially the same mass distribution, moments of inertia and elastic modules about bending axes W—W and W'—W', respectively. The conduits extend outwardly from the manifold in an essentially parallel fashion.

Conduits 103A–103B are driven by driver 104 in opposite directions about their respective bending axes W and W' and at what is termed the first out of phase bending mode of the flowmeter. Driver 104 may comprise any one of many well known arrangements, such as a magnet mounted to conduit 103A and an opposing coil mounted to conduit 103B and through which an alternating current is passed for vibrating both conduits. A suitable drive signal is applied by meter electronics 20, via lead 110, to driver 104.

Meter electronics 20 receives the left and right velocity signals appearing on leads 111' and 111', respectively. Meter electronics 20 produces the drive signal appearing on lead 110 and causing driver 104 to vibrate tubes 103A and 103B. Meter electronics 20 processes the left and right velocity signals to compute the mass flow rate and the density of the material passing through meter assembly 10. This information is applied by meter electronics 20 over path 26 to a utilization means (not shown).

It is known to those skilled in the art that Coriolis flowmeter 5 is quite similar in structure to a vibrating tube densitometer. Vibrating tube densitometers also utilize a vibrating tube through which fluid flows or, in the case of a sample-type densitometer, within which fluid is held. Vibrating tube densitometers also employ a drive system for exciting the conduit to vibrate. Vibrating tube densitometers typically utilize only a single feedback signal since a density measurement requires only the measurement of frequency and a phase measurement is not necessary. The descriptions of the present invention herein apply equally to vibrating tube densitometers.

Figure 2:
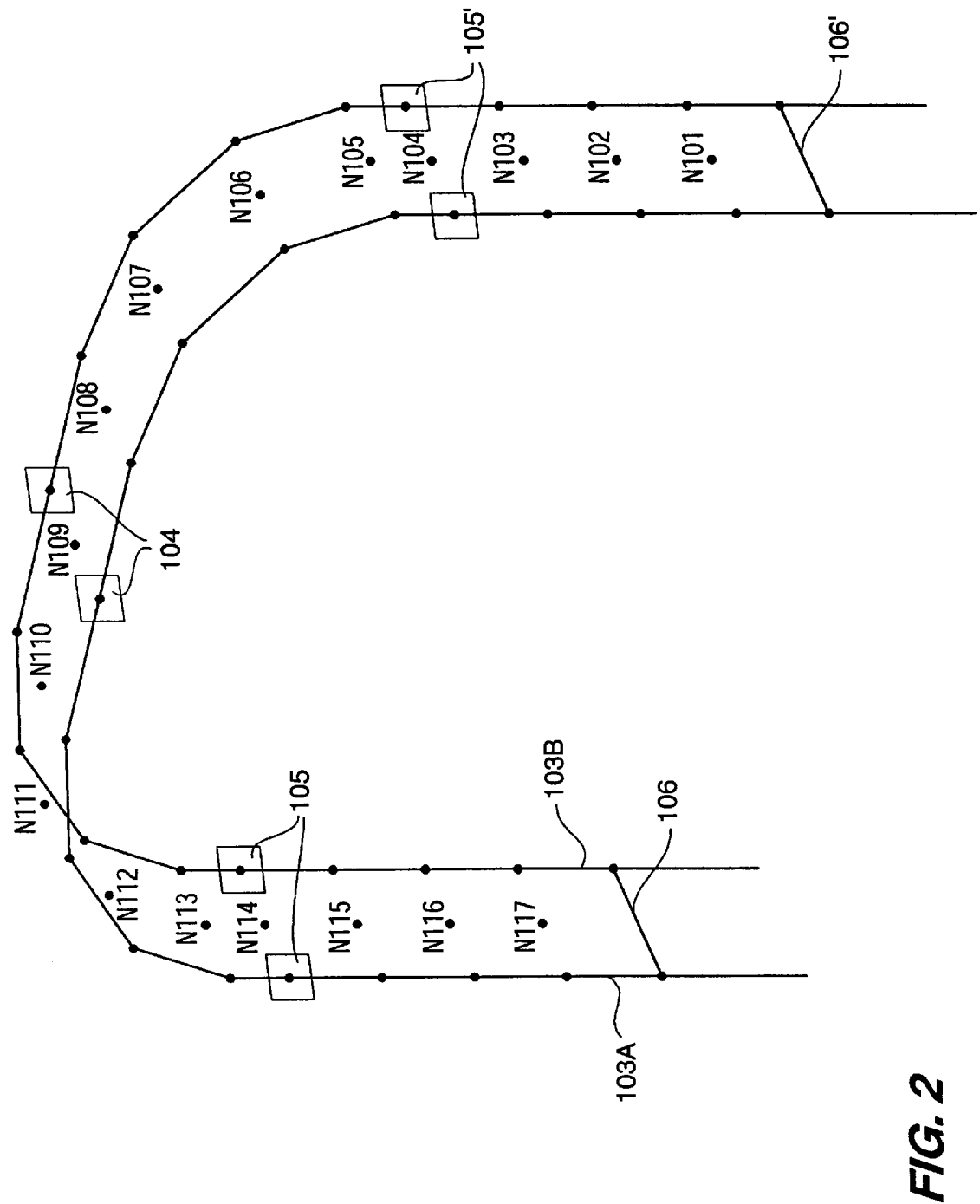
FIG. 2 depicts a finite element model representation of the vibrating conduits of the Coriolis mass flowmeter system of FIG. 1.
Figure 3:
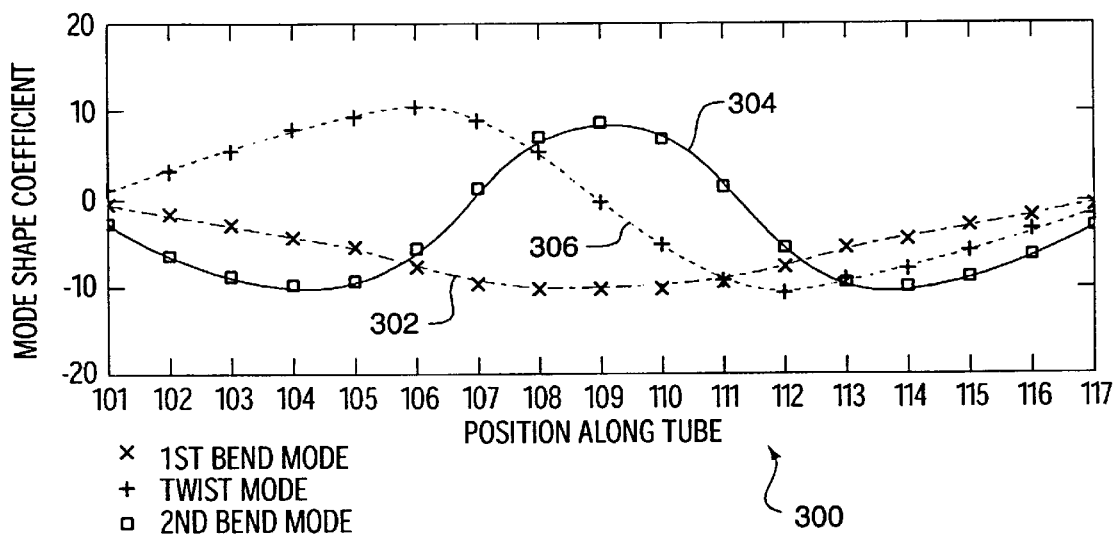
FIG. 3 is a graph of mode shape coefficients with respect to position along the conduits of FIG. 2.

Mode Shape Coefficients—FIGS. 2–3

FIG. 2 depicts a finite element model of conduits 103A–103B of flowmeter 10 depicted in FIG. 1. For purposes of describing the present invention only the vibrating portion of the flowmeter need be discussed, thus FIG. 2 depicts only conduits 103A–103B. The model fixes to ground the ends of the flow tubes that, on a physical flowmeter, connect to the flowmeter manifold. Finite element modeling techniques are well known to those skilled in the art and do not form part of the present invention. The exemplary finite element model was built using SDRC-Ideas and analyzed by MSC/NASTRAN, a finite element code available from MacNeal-Schwendler. Those skilled in the finite element modeling art recognize that any finite element code could alternatively be used. The locations of the pick-offs were modeled to produce output representative of the relative motion between the locations on the flow tube of the magnet and coil corresponding to the right pick-off, the drive and the left pick-off. These "scalar points" are a standard technique in advanced dynamic analysis. See "A Finite Element for the Vibration Analysis of a Fluid-Conveying Timeshenko Beam.", (AIAA Paper 93-1552), for more information on finite element modeling of Coriolis flowmeters. Each scalar point is marked with a node number N101–N117 on FIG. 2. Nodes N101–N117 facilitate further discussion of mode shapes and their interactions along the length of conduits 103A 103B. Driver 104 and pick-offs 105–105' are shown in the same positions as shown in FIG. 1. Driver 104 and pick-offs 105–105' are shown in FIG. 2 and later FIGS. as an element on each conduit. This is because drivers and pick-offs are typically comprised of a coil attached to one conduit and a magnet attached to a second conduit or to a flowmeter case. The position of driver 104 at node N109 is a known and typical driver position for a curved-tube Coriolis meter driven in a bending mode.

FIG. 3 is a graph of normalized eigenvector coefficients for certain vibration modes as a function of position along conduits 103A–B. The vertical axis of graph 300 is the normalized eigenvector coefficient. The horizontal axis of graph 300 is the position along conduits 103A–B as indicated by nodes N101–N117. Graph 300 includes curve 302 which is comprised of the eigenvector coefficients for the first out-of-phase bending mode with respect to the positions of nodes N101–N117. Graph 300 also includes curve 304 which is comprised of the eigenvector coefficients for the second out-of-phase bending mode with respect to the positions of nodes N101–N117. The third set of data comprising graph 300 is curve 306 which is comprised of the eigenvector coefficients for the first out-of-phase twisting mode with respect to the positions of nodes N101–N117.

FIG. 3 represents a qualitative approach to characterizing the mode shapes present on a vibrating conduit. The eigenvector coefficients used to generate curves 302–306 are generated in one of at least two ways. One approach is to build a finite element model of the vibrating structure of interest from which the eigenvector coefficients for the modes of interest are extracted. Another approach is to use experimental modal analysis techniques to determine the eigenvector coefficients from a physical model of a vibrating structure. Finite element modeling and experimental modal analysis techniques are well-known to those skilled in the art of complex mechanics.

Nodes N101 and N117 are near brace bars 106 and 106', respectively. Brace bars 106, 106' connect conduits 103A–B together and therefore are a location of constraint along the length of conduits 103A–B where very little relative motion occurs between the conduits. Thus all three curves 302–306 approach zero amplitude at nodes N101 and N117. Conduits 103A–B are free to oscillate between nodes N101 and N117. The maximum amplitude of oscillation at each node N101–N117 in each mode is indicated by curves 302–306.

FIG. 2 depicts a driver 104 located at node N109. Node N109 is the center of conduits 103A–B meaning it is a position that is equidistant from each brace bar 106 and 106'. This represents the typical driver position historically used to drive curved-conduit Coriolis flowmeter in the first-out-of phase bending mode. Note hat the first out-of-phase bending mode, as indicated by curve 302, reaches a maximum at node N109, the centerpoint of conduits 103A–B. Thus, node N109 is an efficient position at which to excite the first out-of-phase bending mode. In this context, "efficient" means that a relatively large conduit movement results from a relatively small input force. Node N109 is the most efficient position along conduits 103A–B at which to excite the first out-of-phase bending mode. Note, however, on FIG. 3 that node N109 is also a position of maximum amplitude for the second out-of-phase bending mode, as indicated by curve 304. Thus, energy input to conduits 103A–B at node N109 tends to excite both the first and second out-of-phase bending modes. This is an undesirable condition since one typically does not want to excite the second out-of-phase bending mode. As is well-known to those skilled in the art of vibrating tube sensors, any mode that is excited by a driver is also sensed by the pick-offs and certain modes may detrimentally influence a mass flow or density measurement or the generation of an efficient drive signal.

Figure 4:
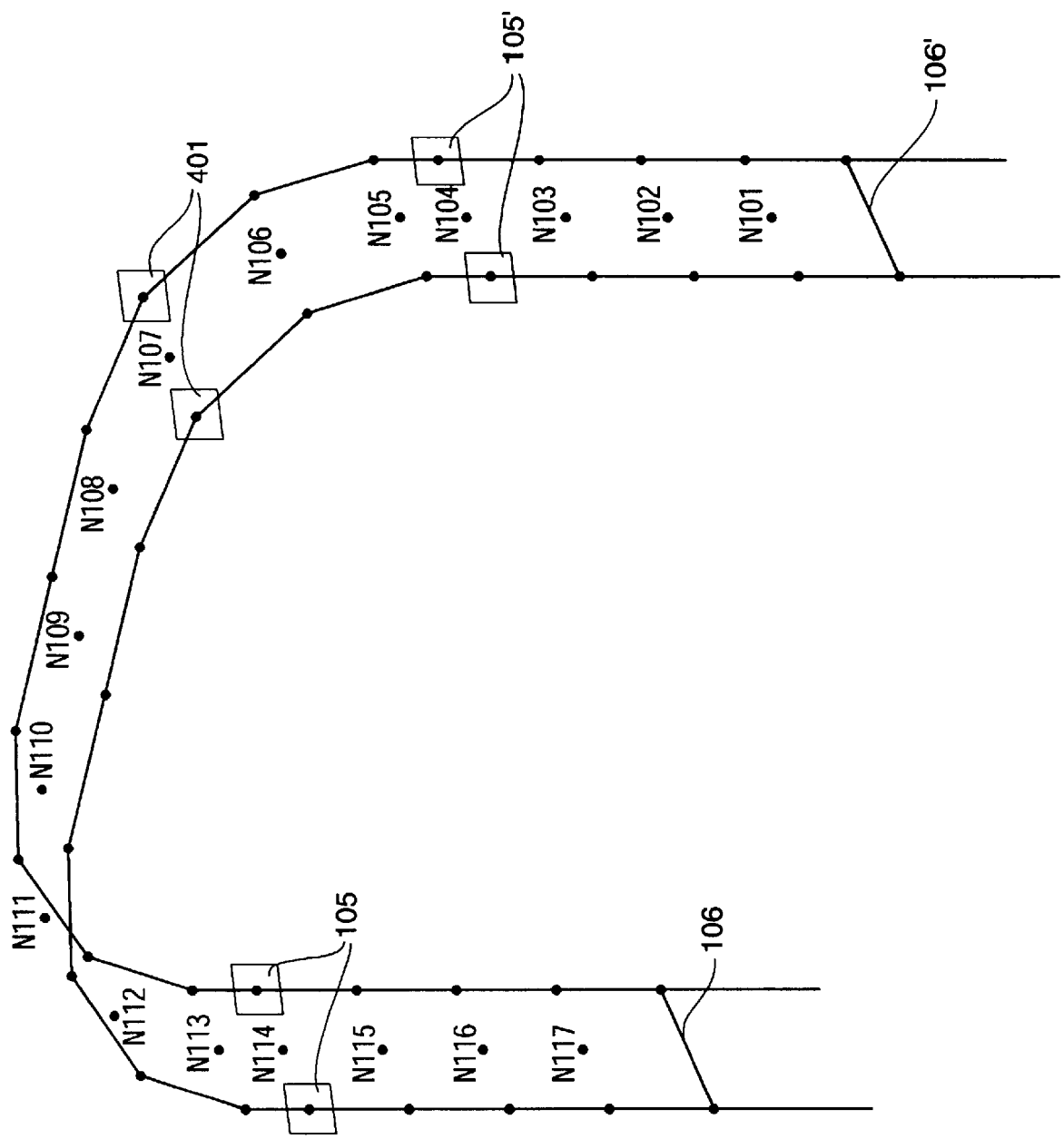
FIG. 4 depicts a finite element model representation of a Coriolis mass flowmeter system including a driver and feedback elements according to the present invention.
Figure 5:
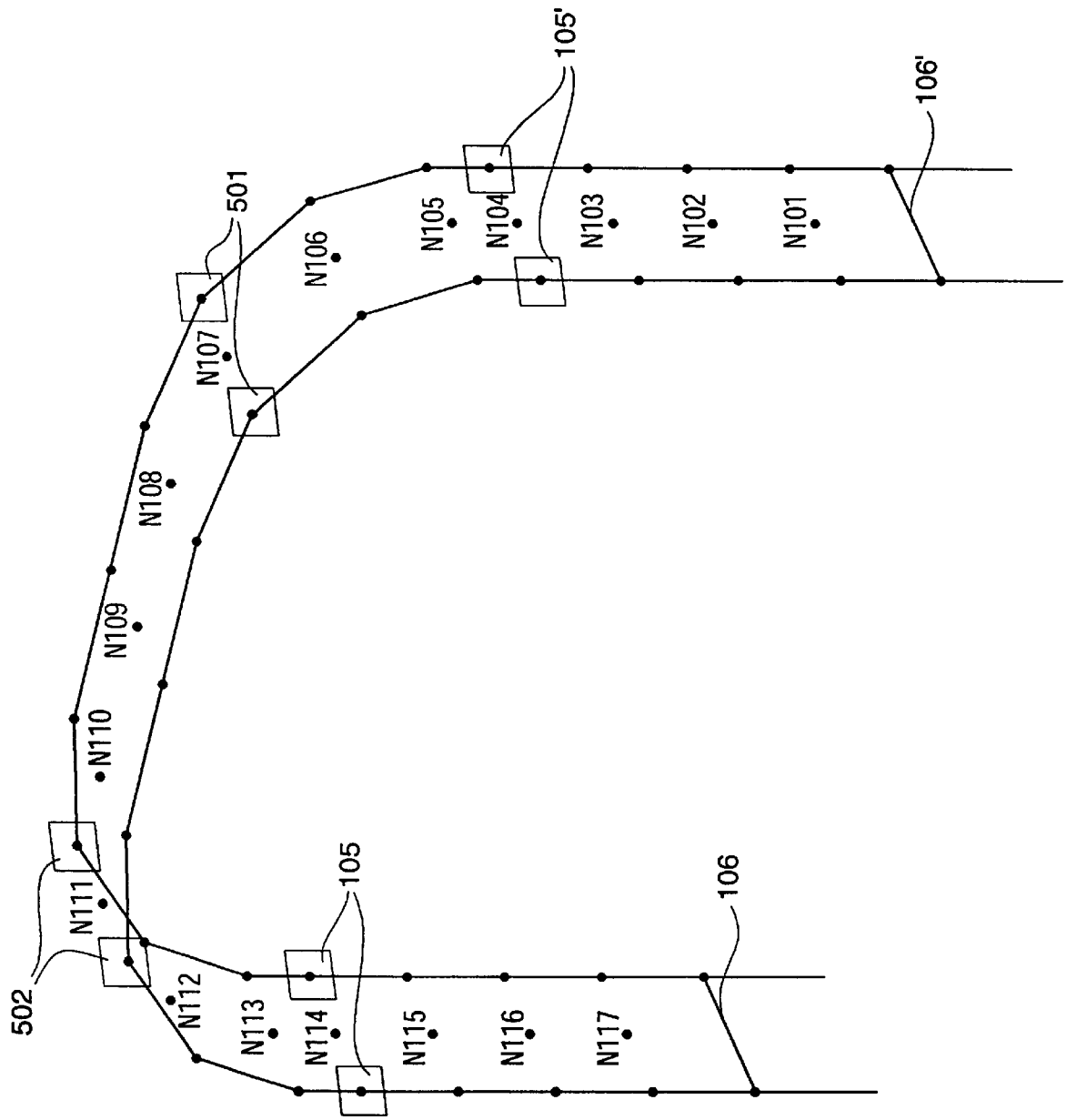
FIG. 5 depicts a finite element model representation of a Coriolis mass flowmeter system including a driver and feedback elements according to another embodiment of the present invention.
Figure 6:
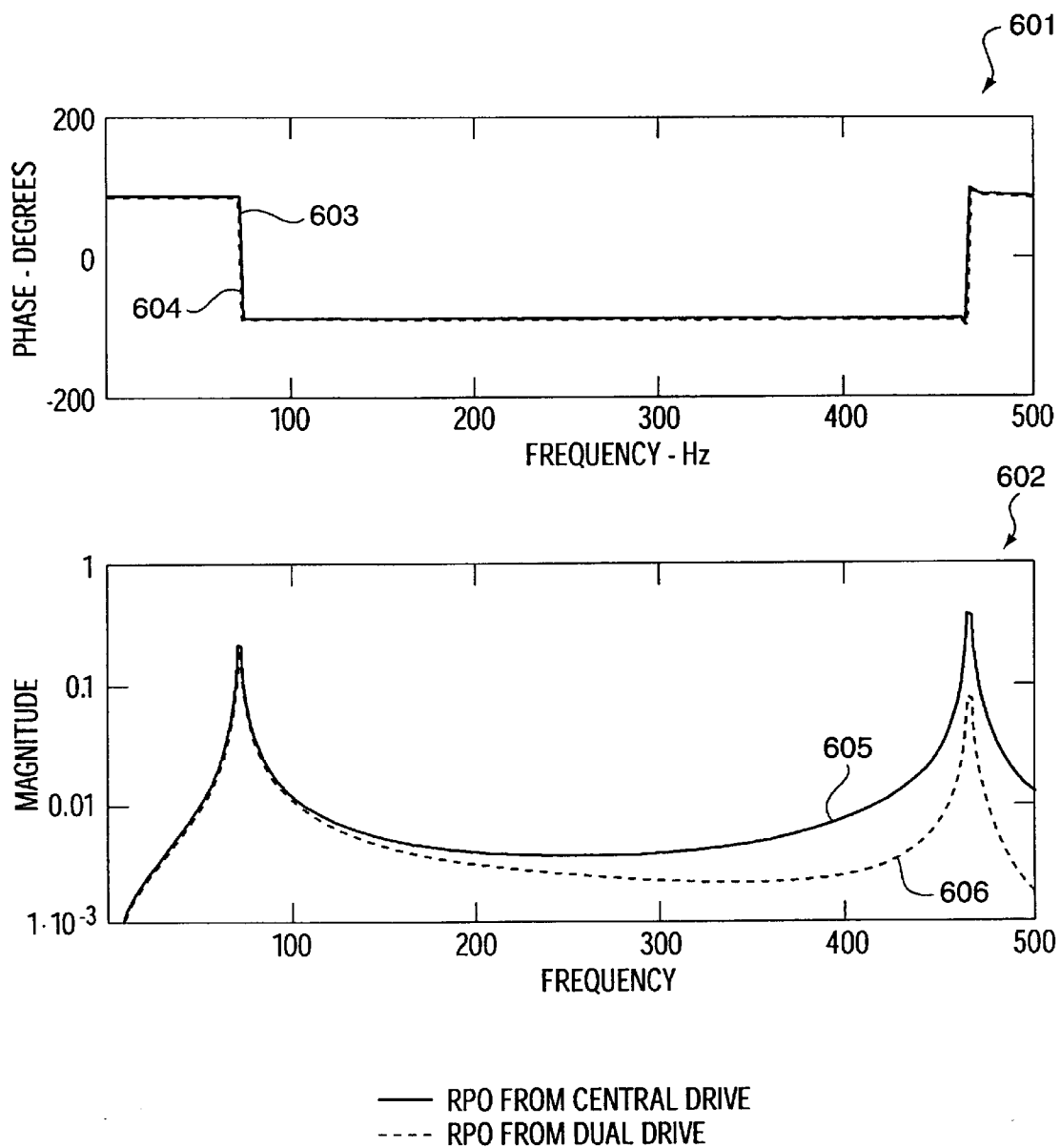
FIG. 6 is a comparison graph of phase and magnitude of conduit velocity for two different driver schemes.

Driver Placement According to the Present Invention—FIGS. 4–6

FIG. 4 depicts conduits 103A–B with a driver 401 located at a position along conduits 103A–B according to the teaching of the present invention. With reference to mode shape coefficient graph 300 of FIG. 3, note that the second out-of-phase bending mode (curve 304) is near a position of minimum amplitude near node N107 while the first out-of-phase bending mode is still near a maximum amplitude at node N107. Energy input to conduits 103A–B at or near node N107 tends, therefore, to excite the first out-of-phase bending mode but not the second out-of-phase bending mode. FIG. 4 shows driver 401 located at node N107. Driver 104, when operated to oscillate conduits 103A–B, excites the first out-of-phase bending mode but does not excite, or minimally excites, the second out-of-phase bending mode. A flowmeter according to the present invention and having one driver, therefore, takes advantage of a knowledge of the various vibration modes present on the vibrating structure to optimally locate the driver so that only the desired drive mode or modes are excited.

The eccentric location of driver 401 gives rise to certain issues. One issue is that energy is input to the vibrating structure in a non-symmetrical fashion due to the eccentric driver location. Also, node N107 is near a position of maximum amplitude of the first out-of-phase twisting mode. Thus, a single driver at node N107 (or the corresponding node N111) tends to eccentrically excite the first out-of-phase twist mode which can be manifested as induced phase shift between two points along conduits 103A–B. Since phase shift between points along the conduit is the basis for the mass flow rate measurement made by a Coriolis flowmeter, this can be a problem.

FIG. 5 depicts two drivers 501–502 located at nodes N107 and N111, respectively. The locations of drivers 501–502, namely nodes N107 and N111, are selected for the same reasons discussed above with respect to FIG. 4 for the case of an eccentrically located single driver. In the case of a flowmeter driven to oscillate in the first out-of-phase bending mode, the force generated by drivers 501–502 is of equal amplitude and phase. With reference to the mode shape coefficient graph 300 of FIG. 3, nodes N107 and N111 are near positions of maximum amplitude for the first out-of-phase bending mode and positions of minimum amplitude for the second out-of-phase bending mode. Thus, the first out-of-phase bending mode is excited and the second out-of-phase bend mode is only minimally excited. In addition, the first out-of-phase twist mode is not excited because drivers 501–502 drive conduit 103A with equal amplitude and equal phase. Therefore, the mass flow rate measurement of the Coriolis flowmeter is not affected as is possible in the embodiment depicted in FIG. 4.

Rather than graphing the eigenvector coefficients as shown in FIG. 3, one can instead use the eigenvector coefficients in combination with the natural frequencies and damping of the vibrating structure to generate a FRF for the vibrating structure. The FRF is used to determine a physical response in inches per second at one location on the vibrating structure to an applied force in pounds at another location on the vibrating structure. This provides a quantitative approach to identifying the optimum driver location. The calculation and manipulation of frequency response functions is well-known to those skilled in the study of vibrating structures.

The FRF matrix, which allows calculating the response at one point of the structure to an input at another point of the structure is given in Equation 1:

$$H(\omega) := \sum_r \frac{\Phi^{(r)} \cdot \Phi^{(r)T} \cdot i \cdot \omega}{(\omega_{n_r})^2 - \omega^2 + i \cdot 2 \cdot \zeta_r \cdot \omega \cdot \omega_{n_r}} \qquad \text{EQN. 1}$$

where $H(\omega)$ is the FRF matrix as a function of frequency in units of response normalized by a unit excitation. Typical units are inches/second per pound. The FRF matrix indices correspond to physical locations for the response and excitation, i.e., $H_{ij}$ is the response at location i to a unit excitation at location j. The summation index r corresponds to the number of modes desired, which is defined by the number of columns in the eigenvector matrix $\Phi$. Each row in $\Phi$ corresponds to the eigenvector coefficient of a physical location in the structure for which a response is desired or at which a force is to be applied. The eigenvector matrix $\Phi$ can be conveniently derived from a finite element analysis or measured experimentally. The i $\omega$ term, where $i=\sqrt{-1}$ indicates that the response is in terms of velocity. The $\omega$ term in the numerator and denominator is the frequency of excitation in radians/second. $\Phi^{(r)}$ is the r'th eigenvector (column of the eigenvector matrix) normalized to unity modal mass. $\zeta$ is the modal damping for the r'th mode as a fraction of critical damping, and $\omega_n$ is the undamped natural frequency of the r'th mode in radians/second.

A physical response, X, to a given force, F, is calculated from Equations 1 and 2. Note that response in this linear system to multiple forces can be superimposed by adding the individual responses to a single force.

$$X(w)=H(\omega)\times F \qquad \text{EQN. 2}$$

Equations 1 and 2 are used to calculate the physical velocity of a first point, for example pick-off 105' at node N113 in FIGS. 2 and 5, in response to a force applied at a second point, i.e., the location of the driver(s). For the case of the conventional drive illustrated in FIG. 2, the force is applied at the centerpoint of conduit 103A, node N109. For the case of the dual drives illustrated in FIG. 5, the orce is applied symmetrically at both nodes N107 and N111. A "symmetrically" applied force is one that is applied at both nodes with equal magnitude and in phase with one another.

FIG. 6 illustrates a comparison of the magnitude and phase of the physical velocity of pick-off 105' for the single and dual drive cases. The data of FIG. 6 is generated from the FRF for the modeled CMF300 flowmeter for both the single and dual drive cases. Graph 601 illustrates the phase of the conduit velocity with respect to frequency at pick-off 105' (node N113). Graph 602 illustrates the magnitude of the conduit velocity with respect to frequency at pick-off 105' (node N113). Curve 603 of graph 601 is the phase of the conduit velocity at node N113 in the case of a single drive located at node N109. Curve 604 of graph 601 is the phase of the conduit velocity at node N113 in the case of dual drives at nodes N107 and N111, respectively. Note that there is no difference in the phase of the conduit velocity between the two cases of single, central drive and dual drives. Curve 605 of graph 602 is the magnitude of the conduit velocity at node N113 in the case of a single drive located at node N109. Curve 606 of graph 602 is the magnitude of the conduit velocity at node N113 in the case of dual drives at nodes N107 and N111, respectively. Note that the response in both cases is the same at the first out-of-phase bending mode at 73 Hz. Note also that the response of the second out-of-phase bending mode, at 466 Hz is a factor of about 5 less for the dual drive case as compared to the conventional, single drive case. This is because the response of the nodes N107 and N111 in the second bending mode is smaller than the response of N109, but it is not completely zero, as shown in FIG. 3. The response of the second bending mode could be reduced even further by moving the location of nodes N107 and N111 to a point where the eigenvector coefficient for this mode is closer to zero. In this case that would mean moving the driver at node N107 towards node N106 and the driver at node N111 towards node N112, for example with reference to FIG. 3. Note also that the total response, the area under curve, for the dual drive case, curve 606 is about half that of the single drive case, curve 605. The lower total response in the dual drive case indicates that the intended mode, i.e., the first out-of-phase bend mode, is more efficiently excited in the dual drive case than in the single drive case. The frequency response function and the resulting graphs of FIG. 6 illustrate a quantitative approach to understanding the advantages of the drive system of the present invention.

Figure 8:
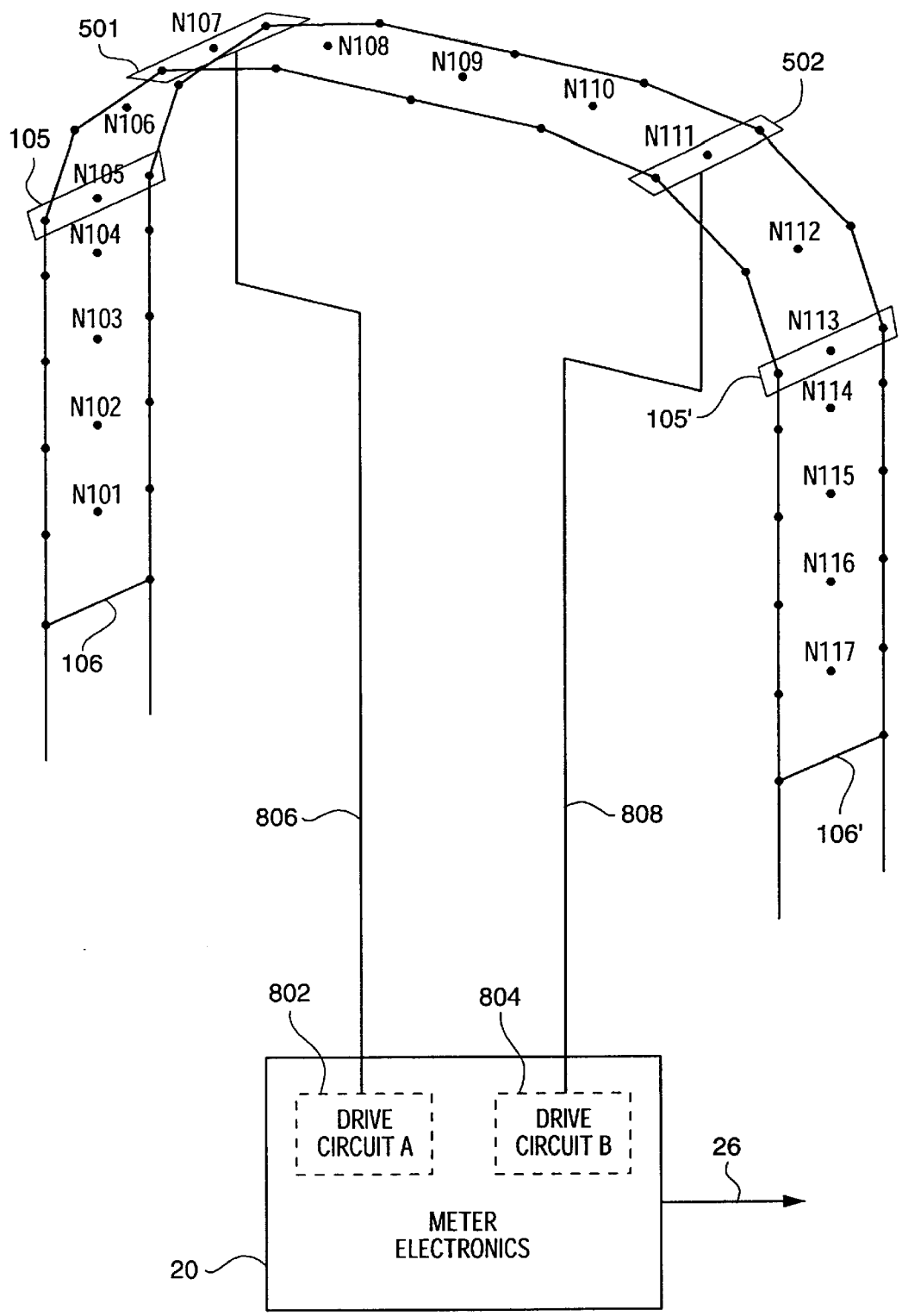
FIG. 8 depicts a dual drive system having electrically isolated drive circuits for each driver element.

Additional Drive Power—FIG. 8

A further advantage of dual drives as described above, in particular with respect to drive scheme of FIG. 5, is the ability to deliver more drive power to conduit 103A. In practice, a driver on a Coriolis mass flowmeter is limited to about 0.5 Watt of power for intrinsic safety reasons. Those skilled in the art of industrial process control are familiar with intrinsic safety requirements. Essentially, these requirements are intended to ensure that a process control device, such as a Coriolis flowmeter, does not expose sufficient energy, either stored or instantaneously, to an explosive environment such that the environment could be ignited. Designers of Coriolis flowmeters are accustomed to trading off (in the case of electromagnetic drivers) drive current, strength of magnetic field and number of turns of coil wire to achieve a suitable driver force. It is sometimes difficult, however, to deliver force to a driver such that the driver sufficiently oscillates the conduit for proper operation of the flowmeter. This is particularly true for larger sized conduits and conduits through which a fluid flows within which is entrained gas. The system of the present invention is used in these conditions to provide additional drive power for vibrating a conduit. If a dual drive system is designed such that the two drivers are each part of electrically isolated drive circuits then each driver can supply approximately 0.5 Watt of drive power to the conduit and still satisfy the necessary intrinsic safety requirements.

FIG. 8 depicts a dual drive system as depicted in FIG. 5 as well as meter electronics 20. Meter electronics 20 includes drive circuit A 802 an drive circuit B 804. Drive circuits 802–804 are electrically isolated from one another and therefore can be treated as separate circuits for purposes of intrinsic safety calculations. Drive circuit A 802 is connected to driver 501 over path 806. Drive circuit B 804 is connected to driver 502 over path 808. Each drive circuit 802–804 provides up to the maximum power allowable under the relevant intrinsic safety requirements to its respective driver 501–502. Thus, each driver 501–502 can provide, for example, 0.5 Watt of driving power to conduit 103A.

Figure 7:
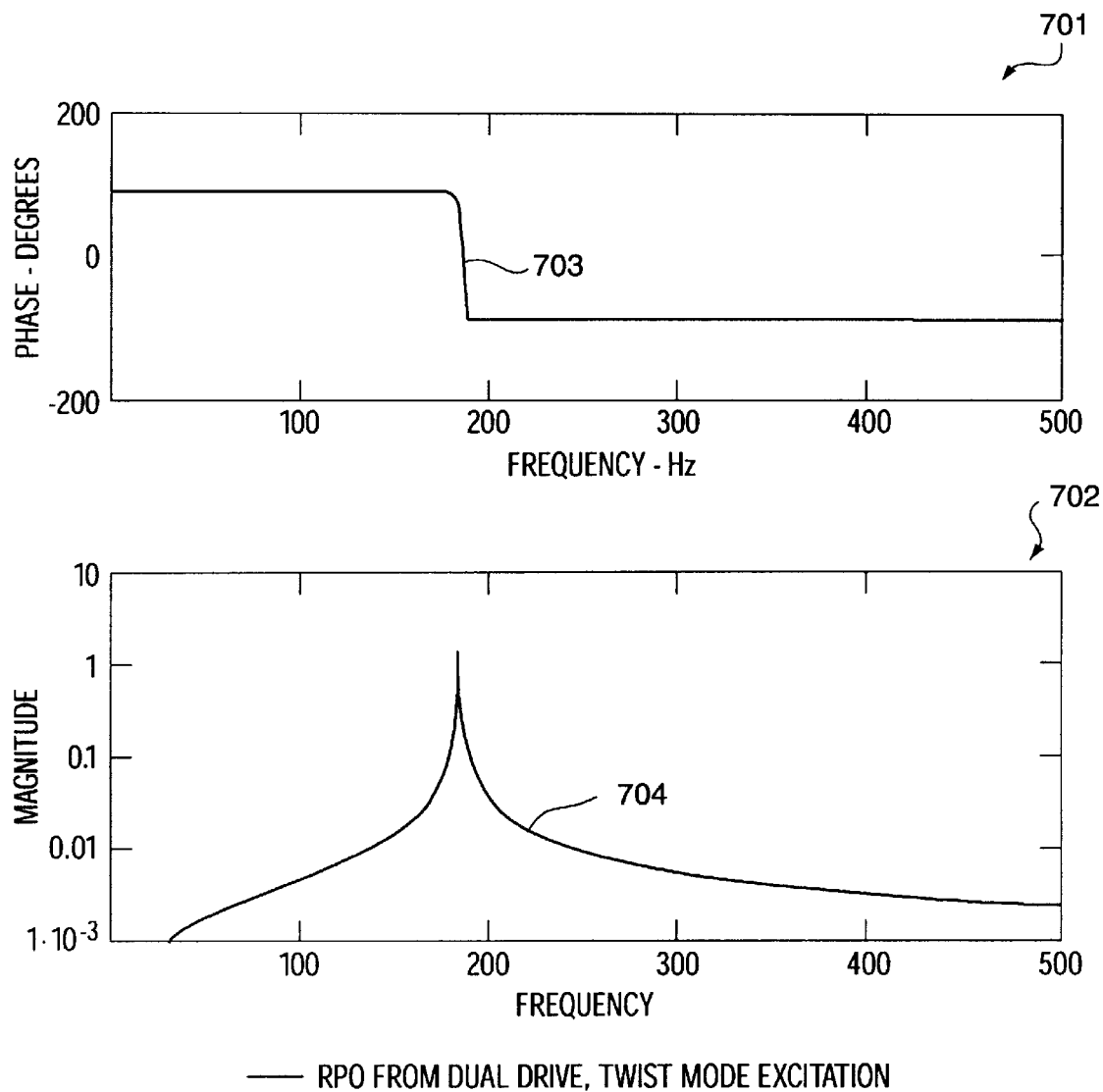
FIG. 7 is a graph of phase and magnitude of conduit velocity for a driver scheme using dual drivers delivering force with equal amplitude but opposite phase.

Exciting Alternate Modes—FIG. 7

Another application of the dual drive system of the present invention is for excitation of alternate modes. As noted above, the first out-of-phase bending mode is the most common driven mode for existing Coriolis mass flowmeters. However, the invention of the present invention is applicable to any conduit geometry and to use of any driven mode or modes. The first out-of-phase twist mode, for example, may be efficiently excited by the drive system of the present invention.

The drive schemes used to generate the data illustrated in FIG. 6 are unable to excite the first out-of-phase twisting mode. The modeled CMF300 flowmeter has a first out-of-phase twisting mode at 184 Hz and, as seen in FIG. 6, neither the single drive nor the dual drive systems generate significant amplitude at this frequency. The single, central drive scheme cannot excite the twist mode. However, the dual driver scheme offer an alternative. The forces at each drive can be made of equal amplitude but of opposite phase. In other words, the dual drivers can be 180° out of phase with each other. When the dual drives are out of phase, the first out-of-phase bending mode is not excited but the first out-of-phase twist mode is excited.

FIG. 7 illustrates the magnitude and phase of the physical velocity of pick-off 105' for the dual drive case where the drives are 180° out of phase with one another. Graph 701 illustrates the phase of the conduit velocity with respect to frequency at pick-off 105' (node N113). Graph 702 illustrates the magnitude of the conduit velocity with respect to frequency at pick-off 105' (node N113). Curve 703 of graph 701 is the phase of the conduit velocity at node N113 in the case of dual drives at nodes N107 and N111, respectively, where the drives have equal amplitude but opposite phase. Curve 704 of graph 702 is the magnitude of the conduit velocity at node N113 in the case of dual drives at nodes N107 and N111, respectively, where the drives have equal amplitude but opposite phase. Note the strong response at 184 Hz, the first out-of-phase twisting mode, and the lack of a response at the first or second out-of-phase twisting modes. Thus the present invention provides a Coriolis flowmeter for driving in the first out-of-twist mode with drivers located for excitation of the twist mode but not the bending modes.

Figure 9:
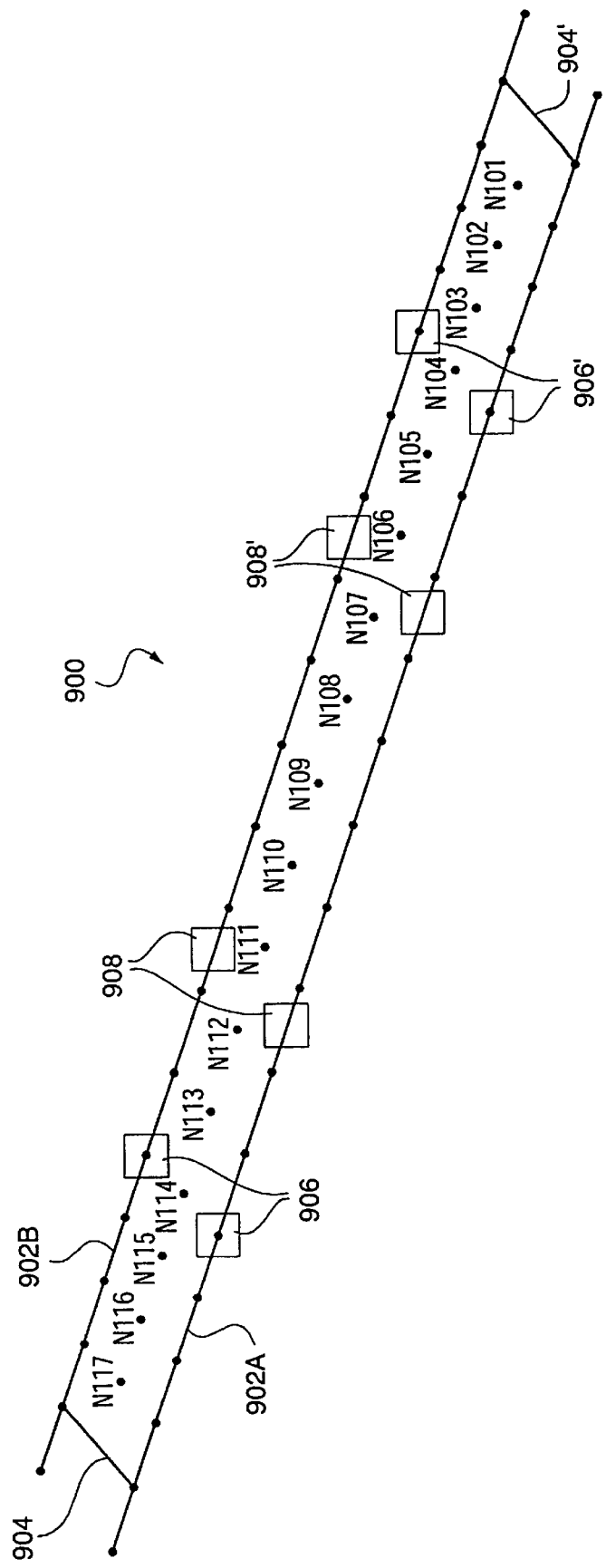
FIG. 9 depicts a finite element model representation of a straight tube Coriolis mass flowmeter according to the present invention.
Figure 10:
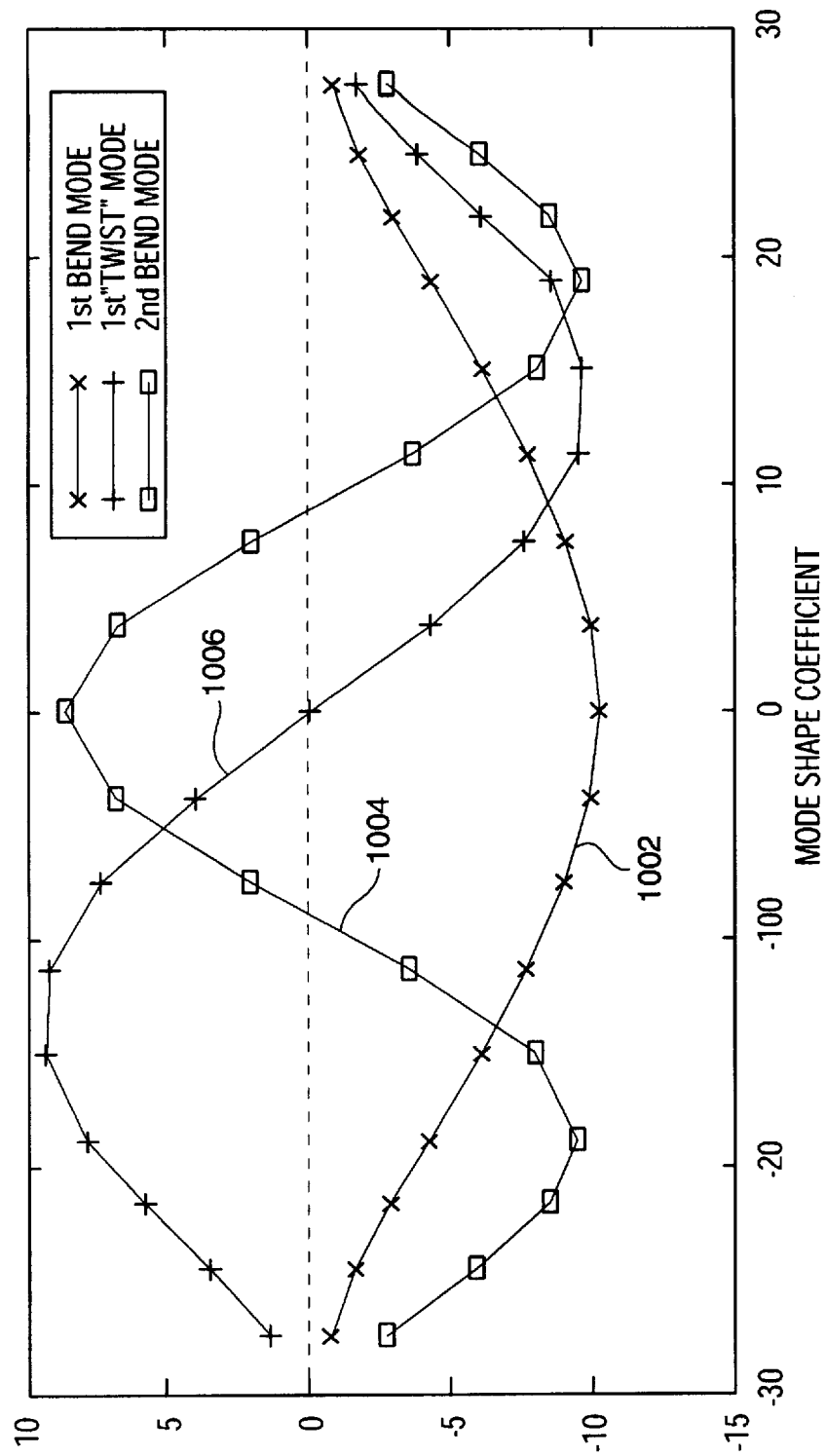
FIG. 10 is a graph of mode shape coefficients with respect to position along the conduits of FIG. 9.

Exemplary Alternate Conduit Geometry—FIGS. 9–10

The teaching of the present invention is not limited to a dual curved-conduit vibrating sensor. Any number of one or more conduits in any geometry configuration can benefit from the driver(s) of the present invention. FIGS. 9–10 provide a further example of the teaching of the present invention.

FIG. 9 depicts a finite element model of a dual-straight-tube Coriolis flowmeter 900. Nodes S101–S117 are indicated along the length of conduits 902A–B. Conduits 902A–B are constrained at each end by brace bar 904 and brace bar 904'. FIG. 10 illustrates mode shape coefficient graph 1000 for flowmeter 900. For the case where one wants to drive flowmeter 900 in the first out-of-phase symmetric bending mode, graph 1000 is examined to locate positions where the first out-of-phase symmetric bending mode is near a maximum amplitude and the second out-of-phase symmetric bending mode is near a minimum amplitude. Curve 1002 represents the eigenvector coefficients for the first out-of-phase symmetric bending mode of flowmeter 900. Curve 1004 represents the eigenvector coefficients for the second out-of-phase asymmetric bending mode of flowmeter 900. Curve 1006 represents the eigenvector coefficients for the first out-of-phase asymmetric bending mode of flowmeter 900.

Examination of mode shape coefficient graph 1000 reveals that roughly midway between node S106 and node S107 the first out-of-phase symmetric bending mode is near a position of maximum amplitude and the second out-of-phase symmetric bending mode is near a position of minimum amplitude. The same is true between nodes S111 and S112. Thus, driver 908 is placed between nodes S106 and S107 and driver 908' is placed between nodes S111 and S112, as shown in FIG. 10. When drivers 908 and 908' are excited with equal amplitude and phase then the first out-of-phase symmetric bending mode is excited and the second out-of-phase symmetric bending mode is not excited or is minimally excited.

FIGS. 9–10 illustrate the breadth of the teaching of the present invention. Although the physical structures depicted in FIGS. 5 and 9 are quite different, the corresponding mode shape coefficient graphs of FIGS. 3 and 10 indicating that the teaching of the present invention is applicable to both. The structures depicted herein are merely exemplary of the teaching of the present invention. The present invention is applicable to any vibrating tube flowmeter or densimeter.

Figure 11:
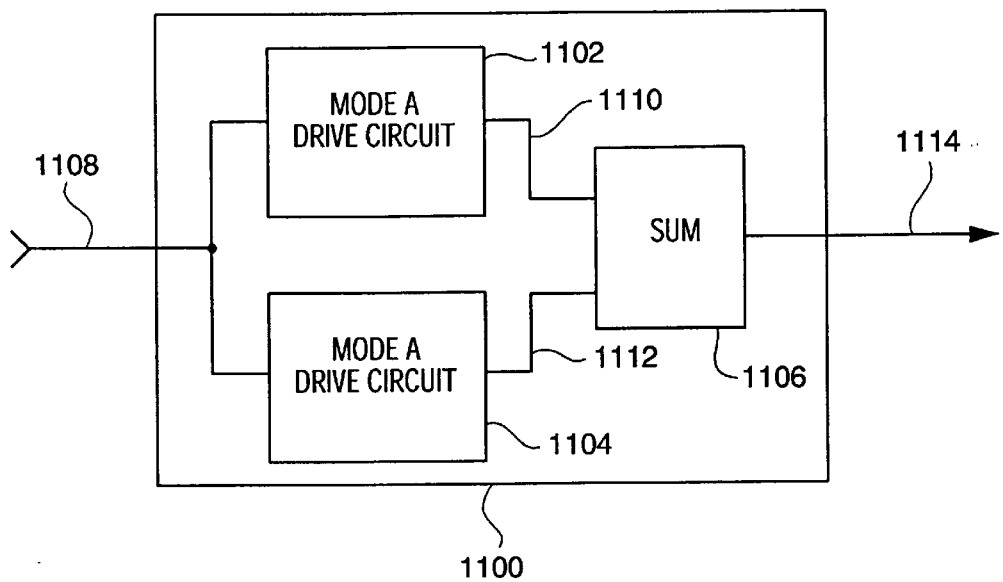
FIG. 11 is a block diagram of a drive circuit for producing a multi-mode drive signal.

Exciting Multiple Modes—FIG. 11

It is sometimes desirable to intentionally excite more than one mode. See for example, copending application Ser. No. 08/689,839 filed Aug. 14, 1996, to assignee Micro Motion, Inc., where two modes are excited and changes in the ratio of the resonant frequencies of the two excited modes are related to fluid pressure within the vibrating conduit. FIG. 11 depicts a block diagram of a drive circuit 1100. Drive circuit 1100 resides, with reference to FIG. 1 or FIG. 8, within a meter electronics 20.

Drive circuit 1100 is comprised of Mode A drive circuit 1102, Mode B drive circuit 1104 and sum stage 1106. Mode A drive circuit 1102 receives a drive feedback signal over path 1108 and produces a drive signal at the frequency of a first mode (Mode A) over path 1110. Mode B drive circuit 1104 receives a drive feedback signal over path 1108 and produces a drive signal at the frequency of a second mode (Mode B) over path 1112. The drive signal over path 1110 from Mode A drive circuit and the drive signal over path 1112 from Mode B drive circuit are input to sum stage 1106. Sum stage 1106 operates to linearly combine the two input drive signals to produce the applied drive signal over path 1114. The applied drive signal over path 1114 is applied to the driver(s) on the vibrating conduit.

Referring now to FIGS. 9–11, assume one wants to excite the flowmeter of FIG. 9 in both the first out-of-phase bending mode (curve 1002) and the first out-of-phase twisting mode (1006). Mode A drive circuit 1102 is configured to produce a first drive signal at the frequency of the first out-of-phase bending mode. Mode B drive circuit 1104 is configured to produce a second drive signal at the frequency of the first out-of-phase twisting mode. The first and second drive signals are summed in sum stage 1106 to produce the applied drive signal over path 1114. The applied drive signal is fed to drivers 908 and 908' on flowmeter 900. Examination of FIG. 10 indicates that drivers 908 and 908' are properly located to excite the first out-of-phase bending mode and the first out-of-phase twisting mode. Drivers 908 and 908' are located between nodes S106 and S107 and S111 and S112, respectively. This is a region of, as noted on FIG. 10, maximum amplitude for both the first out-of-phase twisting mode and the first out-of-phase bending mode and a region of minimum amplitude of the second out-of-phase bending mode. Thus, the multi-mode drive circuit of FIG. 11 excites the first out-of-phase bending mode and the first out-of-phase twisting mode but not the second out-of-phase bending mode.

Those skilled in the art of Coriolis mass flowmeters are familiar with many different ways for generating drive signals by drive circuits 1102 and 1104. See for example, U.S. Pat. No. 5,009,109 issued Apr. 23, 1991 and assigned on its face to Micro Motion, Inc. and copending application Ser. No. 08/890,785 filed Jul. 11, 1997, to applicant Timothy J. Cunningham, which is hereby incorporated by reference to the same extent as though fully disclosed herein.

Although specific embodiments are disclosed herein, it is expected that persons skilled in the art can and will design alternative Coriolis flowmeter drive systems employing driver locations and multiple drivers that are within the scope of the following claims either literally or under the Doctrine of Equivalents.

We claim:

1. A process parameter measurement apparatus having at least one conduit which tends to oscillate in at least one desired mode and at least one undesired mode and a drive system for vibrating said at least one conduit, wherein said drive system comprises:

first drive control means for producing a first drive signal;

a first driver attached to a first location on said at least one conduit and responsive to said first drive signal for causing said at least one conduit to oscillate; and said first location is determined to be a point alone said at least one conduit where application of force from said first driver that substantially maximizes an amplitude of vibrations in said at least one desired mode and that substantially minimizes an amplitude of vibrations in said at least one undesired mode.

2. The drive system of claim 1 wherein said drive control means includes:

means for receiving a first feedback signal from a first pick-off attached to said at least one conduit, said first feedback signal being indicative of the oscillatory movement of said at least one conduit at the location of said first pick-off;

means for conditioning said first feedback signal to generate said first drive signal; and means for applying said first drive signal to said first driver thereby causing said at least one conduit to oscillate.

3. The drive system of claim 2 wherein said conditioning means includes:

a frequency filter for filtering said first feedback signal to produce a frequency-filtered feedback signal having reduced amplitude beyond a roll-off frequency; and amplifier means for amplifying said frequency-filtered feedback signal to produce said first drive signal.

4. The drive system of claim 2 wherein said conditioning means includes:

a modal filter for filtering said first feedback signal to produce a modally-filtered feedback signal having modal content at fewer modes than said first feedback signal; and amplifier means for amplifying said modally-filtered feedback signal to produce said first drive signal.

5. The drive system of claim 1 further comprising:

a second driver attached to a second location on said at least one conduit and responsive to a drive signal for causing said at least one conduit to oscillate; and said first location and said second location are determined to be points along said at least one conduit where application of force to said at least one conduit substantially maximize an amplitude of vibrations in said at least one desired mode and that substantially minimize an amplitude of vibrations in said at least one undesired mode.

6. The drive system of claim 5 wherein said first and second drivers respond to said first drive signal causing said at least one conduit to oscillate.

7. The drive system of claim 6 wherein said at least one desired mode is the first out-of-phase bending mode.

8. The drive system of claim 7 wherein said at least one undesired mode is the second out-of-phase bending mode.

9. The drive system of claim 5 wherein said first driver responds to a first drive signal and said second driver responds to a second drive signal and wherein said first drive signal and second drive signal are of substantially equal magnitude and substantially opposite phase.

10. The drive system of claim 9 wherein said at least one desired mode is the first out-of-phase twist mode.

11. The drive system of claim 9 wherein said at least one undesired mode is the first out-of-phase bending mode.

12. The drive system of claim 1 further comprising:

a second driver attached to a second location on said at least one conduit;

a second drive control means for producing a second drive signal; and said first drive control means and said second drive control means being electrically isolated from one another.

13. The drive system of claim 12 wherein said first and second drive signals have substantially equal amplitude and substantially equal phase.

14. The drive system of claim 12 wherein said first and second drive signals have substantially equal amplitude and substantially different phase.

15. The drive system of claim 1 wherein said process parameter measurement apparatus is a Coriolis mass flowmeter for measuring the mass flow rate of fluid there through.

16. The drive system of claim 1 wherein said process parameter measurement apparatus is a vibrating-type densimeter for measuring the density of fluid therein.

17. A process parameter measurement apparatus having at least one conduit which tends to oscillate in at least one vibration mode, comprising:

first drive control means for producing a first drive signal;

second drive control means for a producing a second drive signal;

a first driver attached to a first location on said at least one conduit and responsive to said first drive signal for causing said at least one conduit to oscillate;

a second driver attached to a second location on said at least one conduit and responsive to said second drive signal for causing said at least one conduit to oscillate;

said first location and said second location being at points along said conduits where application of force at said points substantially maximizes an amplitude of vibration in said at least one desired mode of vibration; and said first drive control means and said second drive control means being electrically isolated from one another.

18. The drive system of claim 17 wherein said process parameter measurement apparatus is a Coriolis mass flowmeter for measuring the mass flow rate of fluid there through.

19. The drive system of claim 17 wherein said process parameter measurement apparatus is a vibrating-type densimeter for measuring the density of fluid therein.

20. A method of operating a drive system for a Coriolis mass flowmeter having at least one conduit which tends to oscillate in at least one desired mode and at least one undesired mode, comprising the steps of:

locating a first driver to a first location on said at least one conduit;

locating a second driver to a second location on said at least one conduit wherein said first location and said second location are points along said conduits that are determined to be points where application of force substantially maximizes an amplitude of vibration in said at least one desired mode and substantially minimizes an amplitude of vibrations in said at least one undesired mode;

producing a drive signal; and applying said drive signal to said first driver and said second driver thereby causing said at least one conduit to oscillate.

21. The method of claim 20 wherein said step of producing a drive signal includes:

producing a first drive signal which is applied to said first driver; and producing a second drive signal which is applied to said second driver.

22. The method of claim 21 wherein said step of producing a drive signal includes:

producing a first drive signal which is applied to said first driver;

producing a second drive signal which is applied to said second driver; and said first drive signal and said second drive signal having substantially equal phase and substantially equal amplitude.

23. The method of claim 21 wherein said step of producing a drive signal includes:

producing a first drive signal which is applied to said first driver;

producing a second drive signal which is applied to said second driver; and said first drive signal and said second drive signal having substantially unequal phase and substantially unequal amplitude.

24. The method of claim 21 wherein said step of producing a drive signal includes:

producing a first drive signal which is applied to said first driver;

producing a second drive signal which is applied to said second driver; and said first drive signal and said second drive signal having substantially unequal phase and substantially equal amplitude.

25. The method of claim 21 wherein said step of producing a drive signal includes:

producing a first drive signal which is applied to said first driver;

producing a second drive signal which is applied to said second driver; and said first drive signal and said second drive signal being electrically isolated from one another.

* * * * *